United States Patent [19]
Brandes et al.

[11] 4,231,966
[45] Nov. 4, 1980

[54] METHOD OF CONDUCTING REACTIONS IN A TRICKEL-TYPE REACTOR

[75] Inventors: Günter Brandes, Hamburg; Johannes Wöllner, Kapellen Krs. Moers; Wilhelm Neier; Werner Webers, both of Orsoy, all of Fed. Rep. of Germany

[73] Assignee: Deutsche Texaco Aktiengesellschaft, Hamburg, Fed. Rep. of Germany

[21] Appl. No.: 953,508

[22] Filed: Oct. 23, 1978

[30] Foreign Application Priority Date
1/30/1974 [DE] Fed. Rep. of Germany .............................. 2404329

Related U.S. Application Data

[62] Division of Ser. No. 545,641, Jan. 30, 1975.

[51] Int. Cl.$^3$ ............................................ C07C 45/45
[52] U.S. Cl. .................................................. 568/396
[58] Field of Search .................................... 260/593 R

[56] References Cited
U.S. PATENT DOCUMENTS 3,574,763  4/1971  Wollner et al. .................. 260/593 R

FOREIGN PATENT DOCUMENTS 1260454  2/1968  Fed. Rep. of Germany ...... 260/593 R

OTHER PUBLICATIONS

Satterfield, A I Chem. E. J., vol. 21 (2), pp. 209–228, (1975).

*Primary Examiner*—Natalie Trousof
*Assistant Examiner*—James H. Reamer
*Attorney, Agent, or Firm*—Carl G. Ries; Robert A. Kulason; Robert Knox, Jr.

[57] ABSTRACT

Trickle-type fixed-bed catalytic reactions are improved, prior to starting or resuming an on-stream period, by purging air from the catalyst bed and reaction zone by downward flow of an inert gas therethrough, flooding the purged reaction zone by flowing a liquid upwardly through the catalyst bed to cover same, then removing the liquid and instituting the on-stream period by introducing gaseous and liquid reactants at the upper end of the catalyst bed to flow downwardly therethrough.

10 Claims, No Drawings

METHOD OF CONDUCTING REACTIONS IN A TRICKEL-TYPE REACTOR

This is a division, of application Ser. No. 545,641, filed Jan. 30, 1975.

This invention relates to the conducting of continuous reactions at elevated temperature and pressure in a trickle-type reactor using a fixed-bed catalyst traversed by gaseous and liquid reactants, particularly in downward cocurrent flow.

Various methods are known for carrying out the above-described type of reactions. For example, German Auslegeschrift No. 1,291,729 discloses the preparation of lower alcohols and ethers by direct hydration of lower olefins in a reactor filled with particles of a sulfonated synthetic resin catalyst in a fixed bed and charged with liquid water and gaseous olefin, especially propylene, at temperatures of 110° to 170° C. and under a pressure of from 60 to 120 atmospheres gauge, advantageously in downward cocurrent flow direction. Other embodiments of this known procedure are disclosed, for example, in German Offenlegungsschriften Nos. 2,147,737, 2,147,738 or 2,147,739.

A further method of this type is disclosed in German Pat. No. 1,260,454, which method is used for preparing higher carbonyl compounds by condensation of lower carbonyl compounds and simultaneous hydrogenation of the unsaturated intermediate product. In this method, the fixed-bed catalyst consists of a strongly acid cation exchange resin which comprises a hydrogenating metal.

In practice, when such reactions are carried out in trickle-type reactors, frequent difficulties occur when the reactor is filled with the catalyst and put into operation, or, when the reaction is interrupted and subsequently operation is resumed. As a rule, the catalyst suspended in a suitable fluid—preferably a liquid reactant—is introduced or slurried into the reactor until the catalyst bed has attained the desired depth in the reactor. After the reactor has been filled with catalyst, the remaining air in the reactor system (in the reactor top and bottom sections as well as between the catalyst grains) must be displaced and removed. This is effected by flushing the reactor with an inert gas or with the gaseous component of the intended reaction.

In case of relatively coarse catalyst particles having an average particle, or grain, diameter of, for example, 4 mm or more, these displacement measures taken in reactor systems do not present any difficulties, but they are frequently ineffective and may even cause damage in the case of fine-grained catalysts where the average catalyst particle size is below 2 or perhaps 1.5 mm. If, for example, a fine-grained catalyst is slurried into the reactor, and an attempt is made to displace the trapped air by flushing the reactor (in upward direction), the air underneath the catalyst bed will push the moist catalyst like a piston and may destroy interior installations, such as intermediate trays and the like, in larger reactors. If, however, the entrapped air is displaced by introducing an (inert) gas at the top of the reactor, this will result in simultaneously displacing the liquid used for slurrying the catalyst as a considerable portion of said liquid is retained by capillary forces in the fine-grained catalyst bed.

It has been shown that a fine-grained catalyst bed which has been freed from air by flushing with inert gas, often no longer is capable of ensuring a uniform distribution of the liquid reactant in the catalyst bed during the subsequent reaction. In fact, zones are formed within the catalyst bed, which are not or are insufficiently traversed by the trickling fluid. This irregular distribution of the liquid often results in the formation of hot spots in the catalyst bed, and the space-time yield and, frequently, the selectivity of the reaction as well as the effective lifetime of the catalyst are seriously affected. It has been found, surprisingly, that these difficulties and the formation of "dry" zones cannot be remedied by spraying the inert gas-flushed catalyst bed with the liquid reactant prior to putting the reactor on-stream. Similar troubles and difficulties are encountered when, after an interruption, the continuous reaction process is to be resumed in such a reactor, even if the reactor was out of operation for only a few hours.

Therefore, it is the object of this invention to provide a method for executing the type of reactions mentioned above which method does not suffer from the described disadvantages and guarantees substantially uniform contact of the catalyst bed with the reactants subsequent to filling fresh catalyst into the reactor or after an interruption of operations.

Our invention provides a process for carrying out reactions between gaseous and liquid reactants where in an on-stream period, the reactants pass in contact with a fixed bed of particulate catalyst in a reaction zone which process comprises prior to instituting the on-stream period removing air from said reaction zone by passing a gas devoid of free oxygen downwardly through said reaction zone and said catalyst bed, interrupting the flow of said gas and introducing a liquid to flow upwardly through said catalyst bed and cover same and then removing said liquid from said reaction zone and substantially simultaneously introducing said gaseous and liquid reactants into said reaction zone to flow downwardly through said catalyst bed and instituting the on-stream period.

In a more specific embodiment these objects are achieved by first filling the reactor in a manner known per se with a fine-grained catalyst in the form of a suspension or slurry to form a catalyst fixed bed of predetermined depth, then purging the fixed bed with an inert gas in downward direction until substantially all of the air has been displaced from the reaction chamber, then flooding the fixed-bed catalyst in upward direction with a suitable liquid medium using conveniently the liquid reactant, and, then, lowering the liquid level in the fixed-bed catalyst by introducing a gas such as an inert gas or more conveniently the gaseous reactant while continuously spraying the bed with the liquid reactant, and starting the reaction.

The method of the invention makes it possible to carry out exothermic reaction processes in trickle columns using very fine granular catalysts with a mean grain size of less than about 2, or even less than about 1.5 mm, in an improved manner. Conveniently, the catalyst bed is purged with about 3 standard liters of inert gas per $cm^2$ of bed cross-sectional area per hour and then liquid is introduced upwardly at a rate of from about 1 to 3 $m^3$ of liquid per $m^2$ of bed cross-sectional area per hour. Although higher flood rates are possible, they may result in incomplete wetting of the catalyst surface. Advantageously the catalyst bed is flooded under elevated pressure, this measure favoring the wetting of "dry" spots in the fixed bed. The flooding under superatmospheric pressure does not usually involve extra costs, since with a new charge being fed to the reactor, a pressure test is ordinarily carried out.

The term "inert gas" when used to describe the purging medium used in the process of our invention is intended to mean a gas which is substantially devoid of free oxygen. Examples of such gases are nitrogen, hydrogen, methane and the like and mixtures thereof.

The method of this invention is described in greater detail in the examples and comparative examples below, describing the production of higher carbonyl compounds such as methyl isobutyl ketone.

EXAMPLE 1

The process described in German Pat. No. 1,260,454 or corresponding U.S. Pat. No. 3,574,763 for the production of methyl isobutyl ketone (MIBK) was carried out in a reactor having a height of 3 m and an inside diameter of 26 mm. One and a half liter of a strongly acid cation exchange resin, specifically a sulfonated styrenedivinyl benzene copolymer (8% divinyl benzene) having a grain size of from 0.3 to 1.2 mm and containing 1.9 wt. % metallic palladium deposited thereon was introduced as a slurry into the reactor.

Before going on-stream, the reactor was purged with nitrogen and the catalyst bed then flooded upwardly with a mixture of 70 volume percent isopropyl alcohol and 30 volume percent MIBK. The liquid level in the reactor was lowered, under spraying with acetone, by introducing hydrogen. The temperature and the hydrogen pressure in the reactor were set to 125° C. and 30 atmospheres gauge, respectively, and the reaction was continued by feeding 3.2 liters of acetone per hour. The reaction product had the following composition:

| | | |
|---|---|---|
| | fore-runnings | 0.5% |
| | acetone | 51.5% |
| | isopropyl alcohol | 0.3% |
| | MIBK* | 38.4% |
| | DIBK** | 1.4% |
| | higher ketones | 0.6% |
| | water | 7.3% |

*methyl isobutyl ketone
**diisobutyl ketone

The space-time yield amounted to 654 grams of MIBK per liter of catalyst volume per hour and the selectivity for MIBK was 93 percent.

EXAMPLE 2

The continuous operation of Example 1 was interrupted for 24 hours. Thereafter, the catalyst bed was sprayed with just 3.2 liters of acetone per hour, which corresponded to a spraying density of about 6 $m^3$ per $m^2$ of reactor cross-sectional area per hour; the reactor was adjusted to the reaction conditions mentioned in Example 5 and operations were resumed. Under otherwise equal conditions, the reaction product now had the following composition:

| | | |
|---|---|---|
| | fore-runnings | 0.6% |
| | acetone | 64.9% |
| | isopropyl alcohol | 0.3% |
| | MIBK | 20.8% |
| | MSO (mesityl oxide) | 0.4% |
| | DIBK | 4.2% |
| | higher ketones | 2.5% |
| | water | 6.3% |

The space-time yield was 400 grams of MIBK per liter per hour and the selectivity for MIBK was 72.2 percent.

EXAMPLE 3

The continuous process of Example 2 was once more interrupted for 24 hours. Subsequently, the catalyst was purged for two hours with hydrogen flowing from the top to the bottom at a rate of 3 liters of hydrogen per $cm^2$ cross-sectional area per hour.

Thereafter, the reactor was flooded upwardly with a mixture consisting of 70 parts by volume of isopropyl alcohol and 30 parts by volume of MIBK at a rate of 1.5 $m^3$ per $m^2$ cross-sectional area per hour. Then the liquid level was lowered and the reactor was adjusted to the operating conditions described in accordance with Example 5. The reaction product had the following composition:

| | | |
|---|---|---|
| | fore-runnings | 0.6% |
| | acetone | 52.9% |
| | isopropyl alcohol | 0.3% |
| | MIBK | 37.0% |
| | MSO | <0.1% |
| | DIBK | 1.5% |
| | higher ketones | 0.6% |
| | water | 7.1% |

The space-time yield derived from the foregoing data amounted to 632 grams of MIBK per liter of catalyst per hour, with a selectivity for MIBK of 92.5 percent.

As shown in the examples, maximum yields and selectivities and uniform temperature distribution are attained when the fixed-bed catalyst, which is free from air or from which the air has been removed, is flooded prior to starting or re-starting the reaction, the flooding step being conveniently conducted under the pressure employed for the reaction, and then the liquid level is lowered under spraying while introducing the gaseous reactant. The superior results attained by following this procedure are not achieved if the flooding step is omitted or if the reactor system is purged with only inert gas or the gaseous reactant to displace the air therefrom even if the fixed bed is sprayed in the aforementioned manner. The successful procedure according to the invention seems to be attributable primarily to flooding the fixed-bed catalyst, conveniently under elevated pressure, prior to the beginning or the resumption of the reaction. The flooding of the fixed-bed catalyst should not, or not appreciably, change the location of the catalyst particles. Movement of the particles is not required nor intended.

Various modifications of the invention as hereinbefore set forth may be made without departing from the spirit and scope thereof, and therefore, only such limitations should be made as are indicated in the appended claims.

The embodiments of the invention in which an exclusive property or privilege is claimed are defined as follows:

1. In a process for carrying out a condensation-hydrogenation reaction between hydrogen and a ketone where in an on-stream period the reactants pass downwardly in contact with a fixed bed of particulate condensation-hydrogenation catalyst having an average particle size no greater than about 2 mm in a trickle-type reaction zone, the improvement which comprises prior to instituting the on-stream period removing air from said reaction zone by passing a gas devoid of free oxygen downwardly through said reaction zone and said catalyst bed, interrupting the flow of said gas and flooding the reaction zone by introducing a liquid to flow upwardly through said catalyst bed and cover same and then removing said liquid from said reaction zone and substantially simultaneously introducing hydrogen and said ketone into said reaction zone to flow downwardly through said catalyst bed under condensation-hydrogenation conditions, thereby instituting the on-stream period.

2. The process of claim 1 in which the ketone is acetone.

3. The process of claim 1 in which to flood the reaction zone, a ketone is passed upwardly at a rate between about 1 and 3 m$^3$ of water per m$^2$ of bed cross-sectional area per hour and the gas devoid of oxygen comprises hydrogen.

4. The process of claim 3 in which the ketone is acetone, the gas devoid of oxygen comprises hydrogen, and the product comprises methyl isobutyl ketone.

5. The process of claim 3 in which the flooding is conducted at substantially the same pressure as the condensation-hydrogenation reaction.

6. The process of claim 1 in which the gas devoid of oxygen is nitrogen.

7. The process of claim 1 in which the gas devoid of oxygen is hydrogen.

8. The process of claim 1 in which the liquid is passed upwardly through said bed at a rate between about 1 and 3 m$^3$ of liquid per m$^2$ of bed cross-sectional area per hour.

9. The process of claim 1 in which the gas devoid of oxygen is passed downwardly through the catalyst bed at a rate of about 3 standard liter per cm$^2$ of bed cross-sectional area per hour.

10. The process of claim 9 in which the particles have an average size no greater than 1.5 mm.

* * * * *